United States Patent
Honda et al.

(10) Patent No.: US 8,580,220 B2
(45) Date of Patent: Nov. 12, 2013

(54) METHOD FOR PRODUCING BIS(FLUOROSULFONYL)IMIDE SALT, METHOD FOR PRODUCING FLUOROSULFATE, AND METHOD FOR PRODUCING BIS(FLUOROSULFONYL)IMIDE ONIUM SALT

(75) Inventors: Tsunetoshi Honda, Akita (JP); Takeshi Kamiya, Akita (JP)

(73) Assignees: Mitsubishi Materials Corporation, Tokyo (JP); Mitsubishi Materials Electronic Chemicals Co., Ltd., Akita-Shi (JP)

( * ) Notice: Subject to any disclaimer, the term of this patent is extended or adjusted under 35 U.S.C. 154(b) by 0 days.

(21) Appl. No.: 13/258,628

(22) PCT Filed: Mar. 30, 2010

(86) PCT No.: PCT/JP2010/002325
§ 371 (c)(1),
(2), (4) Date: Sep. 22, 2011

(87) PCT Pub. No.: WO2010/113483
PCT Pub. Date: Oct. 7, 2010

(65) Prior Publication Data
US 2012/0014859 A1 Jan. 19, 2012

(30) Foreign Application Priority Data

Mar. 31, 2009 (JP) ................................. 2009-084160
Oct. 15, 2009 (JP) ................................. 2009-238344

(51) Int. Cl.
*C01B 21/083* (2006.01)
*C01B 17/45* (2006.01)
*C07C 303/00* (2006.01)

(52) U.S. Cl.
USPC ......................................... 423/386; 423/467

(58) Field of Classification Search
USPC .................................. 423/385–388, 467, 468
See application file for complete search history.

(56) References Cited

FOREIGN PATENT DOCUMENTS

| JP | 08-511274 A | 11/1996 |
|---|---|---|
| JP | 2004-0522681 A | 7/2004 |
| JP | 2007-182410 A | 7/2007 |
| JP | 2009-504790 A | 2/2009 |
| WO | WO 2009123328 A1 * | 10/2009 |

OTHER PUBLICATIONS

Rolf Appel et al., "Synthesis of Imidodisulfuric acid fluoride, $HN(SO_2F)_2$," Institute of Inorganic Chemistry, University of Heidelberg, 95, 1961, pp. 246-248 and English translation thereof (published 1962).
John K. Ruff et al., "Imidodisulfuryl Fluoride, Cesium Imidodisulfuryl Fluoride, and Fluoroimidodisulfuryl Fluoride", Inorganic Syntheses, pp. 138-143 (1968).
John K. Ruff, "The Imidodisulfuryl Fluoride Ion," Inorganic Chemistry, 1965, pp. 1446-1449.
Martin Beran et al., "A New Method of the Preparation of Imidobis(sulfuric acid) Dihalogenide, (F,Cl), and the Potassium Salt of Imido-bis(Sulfuric acid) Difluoride," Z. Anorg. Allg. Chem. 2005, 631, pp. 55-59 and a cover page.
International Search Report dated Jun. 29, 2010, issued for PCT/JP2010/002325 and English translation thereof.

* cited by examiner

*Primary Examiner* — Steven Bos
*Assistant Examiner* — Justin Bova
(74) *Attorney, Agent, or Firm* — Edwards Wildman Palmer LLP; James E. Armstrong, IV; Nicholas J. DiCeglie, Jr.

(57) ABSTRACT

According to the method for producing bis(fluorosulfonyl)imide salt of the present invention, the method for producing fluorosulfate, and the method for producing bis(fluorosulfonyl)imide onium salt, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. In the methods, bis(fluorosulfonyl)imide salt, fluorosulfate, and bis(fluorosulfonyl)imide onium salt can be obtained safely and easily.

9 Claims, No Drawings

METHOD FOR PRODUCING BIS(FLUOROSULFONYL)IMIDE SALT, METHOD FOR PRODUCING FLUOROSULFATE, AND METHOD FOR PRODUCING BIS(FLUOROSULFONYL)IMIDE ONIUM SALT

TECHNICAL FIELD

The present invention relates to a method for producing bis(fluorosulfonyl)imide salt, a method for producing fluorosulfate, and a method for producing bis(fluorosulfonyl)imide onium salt.

Priority is claimed on Japanese Patent Application No. 2009-084160, filed Mar. 31, 2009, and Japanese Patent Application No. 2009-238344, filed Oct. 15, 2009, the content of which is incorporated herein by reference.

BACKGROUND ART

It has been known that bis(fluorosulfonyl)imide salt (($FSO_2)_2$N.M, wherein M is Li, K, $NH_4$, or the like) is a useful anion source for ion electrical conducting materials and ion liquids. Also, it has been known that fluorosulfate is a useful compound used for ion electrical conducting materials and fire-retardant materials. In addition, it has been known that bis(fluorosulfonyl)imide onium salt is a useful ionic compound as an ionic liquid.

As a method for producing bis(fluorosulfonyl)imide, the methods disclosed in NPL1 and NPL2 have been known. More specifically, in NPL1, a method, in which urea (CO$(NH_2)_2$) and fluorosulfonic acid ($FSO_3H$) are mixed first, and then the resulting mixture is heated, allowing the chemical reaction between them to proceed, is disclosed. In this reaction, the chemical reaction represented by the formula (1) below proceeds, producing bis(fluorosulfonyl)imide, ammonium hydrogen sulfate ($NH_4HSO_4$), hydrogen fluoride (HF), and carbon dioxide ($CO_2$).

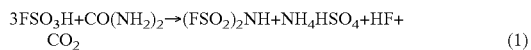

$$3FSO_3H+CO(NH_2)_2 \rightarrow (FSO_2)_2NH+NH_4HSO_4+HF+CO_2 \quad (1)$$

By distilling under reduced pressure during the reaction, a mixed liquid consisting of the newly produced bis(fluorosulfonyl)imide and fluorosulfonic acid is fractionally distilled. By distilling the obtained mixed liquid further, bis(fluorosulfonyl)imide can be recovered.

In NPL2, a method, in which bis(chlorosulfonyl)imide (($ClSO_2)_2NH$) and arsenic trifluoride ($AsF_3$) are reacted, is disclosed. In this reaction, the chemical reaction represented by the formula (2) below is allowed to proceed, producing bis(fluorosulfonyl)imide and arsenic trichloride ($AsCl_3$).

$$3(ClSO_2)_2NH+2AsF_3 \rightarrow 3(FSO_2)_2NH+2AsCl_3 \quad (2)$$

After the reaction, the newly produced bis(fluorosulfonyl)amide is dissolved in dichloromethane. The fraction of the newly produced bis(fluorosulfonyl)amide contain fluorosulfonic acid as an impurity. The contaminating fluorosulfonic acid can also be dissolved in dichloromethane. By adding NaCl to the dichloromethane dissolving bis(fluorosulfonyl)amide and fluorosulfonic acid, the chemical reaction represented by the formula (3) below is allowed to proceed, producing sodium salt of fluorosulfonic acid ($FSO_3Na$) and hydrogen chloride (HCl). Bis(fluorosulfonyl)imide can be recovered by distilling away dichloromethane, after removing the precipitated sodium salt of fluorosulfonic acid.

$$FSO_3H+NaCl \rightarrow FSO_3Na+HCl \quad (3)$$

As a conventional method for producing bis(fluorosulfonyl)amide salt, a method, in which bis(fluorosulfonyl)imide is produced by the methods disclosed in NPL1 and NPL2, and is neutralized by an alkaline compound after dissolving the recovered bis(fluorosulfonyl)imide in water or the like, has been known, as described in NPL3.

As a conventional method for producing fluorosulfate, a method utilizing the chemical reaction represented by the formula (3) has been known. In the method, the bis(fluorosulfonyl)imide produced by the methods disclosed in NPL1 and NPL2. The bis(fluorosulfonyl)amide fraction containing fluorosulfonic acid is dissolved in a solvent, such as dichloromethane or the like, and reacted with NaCl, producing fluorosulfate.

As a conventional method for producing bis(fluorosulfonyl)amide onium salt, a method, in which bis(fluorosulfonyl)imide is produced by the methods disclosed in NPL1 and NPL2, and an onium compound is added to the bis(fluorosulfonyl)imide after dissolving the bis(fluorosulfonyl)imide in water or the like, has been known.

RELATED ART DOCUMENT

Non-Patent Literature

[NPL1] Chem. Bet 95, 246-8 (1962) (Appel&Eisenhauer)
[NPL2] Inorg. Synth. 11, 138-43 (1968)
[NPL3] Inorganic Chemistry Vol. 4, 10, 1446-1449 (1965)

DISCLOSURE OF INVENTION

Technical Problem

In producing bis(fluorosulfonyl)imide, the methods using urea and fluorosulfonic acid is industrially advantageous, since it takes short period of time for the reaction process and the precursors for the reaction is inexpensive. However, it is known that the fluorosulfonic acid, which is one of the raw materials for the reaction, is an extremely strong acid, and sulfuric acid and hydrogen fluoride are formed when a part of the fluorosulfonic acid is degraded in the method disclosed in NPL1 where urea and fluorosulfonic acid are used. As a result, commonly used apparatuses made of glass or metal are corroded by the reaction liquid, when the mixed liquid of bis(fluorosulfonyl)amid and fluorosulfonic acid is recovered from the reaction liquid produced from the chemical reaction represented by the formula (1), by distilling under reduced pressure.

In addition, in the method disclosed in NPL1, in which bis(fluorosulfonyl)imide and fluorosulfonic acid in the mixture are separated by distillation, the separation of the bis(fluorosulfonyl)imide from the fluorosulfonic acid is difficult, since the boiling point of bis(fluorosulfonyl)imide (170° C.) is close to that of fluorosulfonic acid (163° C.).

In the method for recovering bis(fluorosulfonyl)imide (that is, a method for producing sodium salt of fluorosulfonic acid) disclosed in NPL2, the apparatus for the production is corroded by a large amount of hydrogen chloride gas produced as a by-product. In addition, disposing the sodium salt of fluorosulfonic acid separated by straining is difficult, since hydrogen chloride gas evaporates for several days.

In the conventional method for producing bis(fluorosulfonyl)imide salt disclosed in NPL3, the bis(fluorosulfonyl)imide salt is contaminated by impurities such as fluoride ions or the like, since part of the bis(fluorosulfonyl)imide salt undergoes hydrolysis during the process of distilling away of water.

As a result, it is difficult to recover bis(fluorosulfonyl)imide salt having a high purity in the method disclosed in NPL3.

The present invention was made under circumstances described above. The purpose of the present invention is to provide a method for producing bis(fluorosulfonyl)imide salt that enables a highly pure bis(fluorosulfonyl)imide salt to be recovered, safely and easily.

Another purpose of the present invention is to provide a method for producing fluorosulfonic acid safely and easily.

Another purpose of the present invention is to provide a method for producing bis(fluorosulfonyl)imide onium salt safely and easily.

Solution to Problem

After intensive research, the inventors of the present invention found the following. In the presence of bis(fluorosulfonyl)imide, fluorosulfonic acid can be dissolved in water. By neutralizing the water dissolving the mixed liquid consisting of bis(fluorosulfonyl)imide and fluorosulfate, with an alkaline compound, bis(fluorosulfonyl)imide salt and fluorosulfonic acid can be recovered. Particularly, in case of the bis(fluorosulfonyl)imide salt or the fluorosulfonic acid having a low solubility in the neutralized solution, they are precipitated and separated from the neutralized solution. Thus, the intended salts can be obtained by a separation process using a separation funnel, filtration, or the like.

The first aspect of the present invention is a method for producing bis(fluorosulfonyl)imide salt comprising: a step of dissolving, in which a mixed liquid containing bis(fluorosulfonyl)imide and fluorosulfonic acid is dissolved in water to prepare an aqueous solution; a step of neutralizing, in which the aqueous solution is neutralized by an alkali compound to prepare a neutralized solution; and a step of recovering bis(fluorosulfonyl)imide salt, in which bis(fluorosulfonyl)imide salt is recovered from the neutralized solution. In the method, bis(fluorosulfonyl)imide salt may be recovered in the step of recovering bis(fluorosulfonyl)imide salt by extracting the neutralized solution with an organic solvent. Also, in the method, the mixed liquid dissolved in water in the step of dissolving may be a reaction liquid produced by a reaction between urea and fluorosulfonic acid. Also, in the method, the alkaline compound used in the step of neutralizing may be one compound selected from the group consisting of MOH, $M_2CO_3$, $MHCO_3$, ammonia, and amine, wherein M in the chemical formulae, represents one selected from the group consisting Na, K, Li, and ammonium cation.

Also, in the method, a content amount of fluorine ion in bis(fluorosulfonyl)imide salt after the step of recovery may be 100 ppm or less. Also, in the method, a content amount of fluorine ion in bis(fluorosulfonyl)imide salt after the step of recovery may be 20 ppm or less.

The second aspect of the present invention is a method for producing fluorosulfate comprising: a step of dissolving, in which a mixed liquid containing bis(fluorosulfonyl)imide and fluorosulfonic acid is dissolved in water to prepare an aqueous solution; a step of neutralizing, in which the aqueous solution is neutralized by an alkali compound to prepare a neutralized solution; and a step of recovering fluorosulfate, in which fluorosulfate is recovered from the neutralized solution. In the method, fluorosulfate may be recovered in the step of recovering fluorosulfate by straining fluorosulfate precipitated in the neutralized solution. Also, in the method, the mixed liquid dissolved in water in the step of dissolving may be a reaction liquid produced by a reaction between urea and fluorosulfonic acid. Also, in the method, the alkaline compound used in the step of neutralizing may be one compound selected from a group consisting of MOH, $M_2CO_3$, $MHCO_3$, ammonia, and amine, wherein M in the chemical formulae, represents one selected from a group consisting of Na, K, Li, and ammonium cation.

The third aspect of the present invention is a method for producing bis(fluorosulfonyl)imide onium salt comprising: a step of dissolving, in which a mixed liquid containing bis(fluorosulfonyl)imide and fluorosulfonic acid is dissolved in water to prepare an aqueous solution; a step of neutralizing, in which the aqueous solution is neutralized by an alkali compound to prepare a neutralized solution; and a step of adding an onium compound to the neutralized solution. In the method, the mixed liquid dissolved in water in the step of dissolving may be a reaction liquid produced by a reaction between urea and fluorosulfonic acid. Also, in the method, the alkaline compound used in the step of neutralizing may be one compound selected from the group consisting of MOH, $M_2CO_3$, $MHCO_3$, ammonia, and amine, wherein M in the chemical formulae, represents one selected from the group consisting Na, K, Li, and ammonium cation.

Advantageous Effects of Invention

According to the method for producing bis(fluorosulfonyl)imide salt of the present invention, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By recovering bis(fluorosulfonyl)imide salt from the neutralized solution, a highly pure bis(fluorosulfonyl)imide salt can be obtained safely and easily.

In the case where the bis(fluorosulfonyl)imide salt is dissolved in the neutralized solution, the bis(fluorosulfonyl)imide salt can be extracted from the neutralized solution by an organic solvent. In this way, the bis(fluorosulfonyl)imide salt alone can be selectively separated from the neutralized solution.

According to the method for producing fluorosulfate of the present invention, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By recovering fluorosulfate from the neutralized solution, a highly pure fluorosulfate can be obtained safely and easily.

In the case where the fluorosulfate is precipitated in the neutralized solution, the fluorosulfate can be separated by filtering the neutralized solution. In this way, the fluorosulfate alone can be separated from the neutralized solution selectively.

According to the method for producing bis(fluorosulfonyl)imide onium salt of the present invention, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By adding an onium compound to the neutralized solution and changing salts of the bis(fluorosulfonyl)imide salt in the neutralized solution, the bis(fluorosulfonyl)imide onium salt can be obtained safely and easily.

BEST MODE FOR CARRYING OUT THE INVENTION

The method for producing bis(fluorosulfonyl)imide salt, the method for producing fluorosulfate, and the method for producing bis(fluorosulfonyl)imide onium salt of the present invention are explained in detail below.

[Method for Producing bis(fluorosulfonyl)imide salt]

The method for producing bis(fluorosulfonyl)imide salt of the present invention includes, a step of dissolving, in which a mixed liquid containing bis(fluorosulfonyl)imide and fluorosulfonic acid is dissolved in water to prepare an aqueous solution (step of preparing an aqueous solution), a step of neutralizing, in which the aqueous solution is neutralized by an alkali compound to prepare a neutralized solution (step of preparing a neutralized solution), and a step of recovering bis(fluorosulfonyl)imide salt, in which bis(fluorosulfonyl)imide salt is recovered from the neutralized solution (step of recovering). Each step is explained in detail below.

[Step of Preparing an Aqueous Solution]

In the step of preparing an aqueous solution, first, a mixed liquid containing bis(fluorosulfonyl)imide and fluorosulfate is obtained. It is preferable that the mixed liquid containing bis(fluorosulfonyl)imide and fluorosulfonic acid is a reaction liquid between urea ($CO(NH_2)_2$) and fluorosulfonic acid ($FSO_3H$), even though it is not particularly limited to this configuration.

For the reaction between urea ($CO(NH_2)_2$) and fluorosulfonic acid ($FSO_3H$), the conventional reaction represented in the formula (4) disclosed in NPL1, shown below, can be employed.

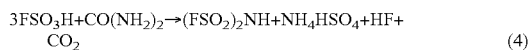

$$3FSO_3H+CO(NH_2)_2 \rightarrow (FSO_2)_2NH+NH_4HSO_4+HF+CO_2 \qquad (4)$$

By distilling under reduced pressure during the reaction represented by the formula (4), a mixed liquid consisting of the newly produced bis(fluorosulfonyl)imide and fluorosulfonic acid, which is a precursor of the reaction, can be fractionally distilled.

The present embodiment is not limited by the method to obtain bis(fluorosulfonyl)imide and fluorosulfonic acid based on the method disclosed in NPL1, and they can be obtained by another chemical reaction.

After obtaining the mixed liquid containing bis(fluorosulfonyl)imide and fluorosulfonic acid, the mixed liquid is dissolved in water. A preferable amount of the water ranges from 1 to 50 parts by mass corresponding to that of the mixed liquid. More preferable amount of the water ranges from 2 to 10 parts by mass corresponding to that of the mixed liquid.

Normally, in the case where fluorosulfonic acid has contacted to water, fluorosulfonic acid reacts extremely vigorously, decomposing it to hydrogen fluoride and sulfuric acid. However, in the method described in this embodiment of the present invention, contacting fluorosulfonic acid with water does not cause the extremely vigorous decomposing reaction. It is interpreted that this inertness of fluorosulfonic acid against water is due to the presence of ammonia or the like, which is formed by decomposition of bis(fluorosulfonyl)imide or urea, in the final reaction solution produced by the reaction between urea and fluorosulfonic acid. The presence of ammonia is believed to extremely reduce the rate of decomposition of fluorosulfonic acid in water. As a result, in this embodiment of the present invention, an aqueous solution dissolving the mixed liquid consisting bis(fluorosulfonyl)imide and fluorosulfonic acid, can be prepared in a mild condition.

[Step of Preparing a Neutralized Solution]

Then, the above-mentioned aqueous solution is neutralized by an alkaline solution quickly, to prepare a neutralized solution. A preferable pH of the neutralized solution at the end ranges from 4 to 10. More preferable pH of the neutralized solution at the end ranges from 7 to 9. It is not preferable for the neutralized solution to have a pH under 4, since production of fluorosulfate and bis(fluorosulfonyl)imide salt is insufficient. It is not preferable for the pH to be over 10, since the decomposition of fluorosulfate and bis(fluorosulfonyl)imide salt is allowed to proceed. By the neutralized solution having a pH in the preferable ranges, the production of fluorosulfate and bis(fluorosulfonyl)imide salt is sufficient, and the decomposition thereof can be suppressed. Thus they are preferable.

The alkaline solution used for neutralizing the aqueous solution can be an aqueous solution containing an alkaline compound selected from the group consisting of MOH, $M_2CO_3$, $MHCO_3$, ammonia ($NH_3$), and amine ($NR_1R_2R_3$), wherein M in the chemical formulae, represents one selected from the group consisting Na, K, Li, and ammonium cation.

As a more specific example of the alkaline compound, sodium hydroxide (NaOH), potassium hydroxide (KOH), lithium hydroxide (LiOH), ammonium hydroxide ($R_1R_2R_3R_4NOH$), sodium carbonate ($Na_2CO_3$), potassium carbonate ($K_2CO_3$), lithium carbonate ($Li_2CO_3$), sodium bicarbonate ($NaHCO_3$), potassium bicarbonate ($KHCO_3$), lithium bicarbonate ($LiHCO_3$), ammonium bicarbonate (($R_1R_2R_3R_4N$)$HCO_3$), ammonia ($NH_3$), or the like can be used.

The ammonium cation ($R_4$—$N^+R_1R_2R_3$) is not particularly limited, and can be any one of the ammonium ion, the primary ammonium cation, the secondary ammonium cation, the tertiary ammonium cation, and the quaternary ammonium cation. Each of $R_1$, $R_2$, $R_3$, and $R_4$ represents a hydrogen atom (H), and an aliphatic or an aromatic alkyl group. In the present embodiment of the present invention, a mixture of alkyl groups selected from the group consisting of methyl-, ethyl-, butyl-, pentyl-, hexyl-, octyl-, decyl-, dodecyl-, tetradecyl-, hexadecyl-, octadecyl-, octadecenyl-, octadecadienyl-, phenyl-groups, or the like can be used.

The amine can be the primary amine, the secondary amine, or the tertiary amine. Selection of the primary amine is not particularly limited, and it can be ethylamine, n-propylamine, iso-propylamine, n-butylamine, iso-butylamine, sec-butylamine, t-butylamine, ethanolamine, n-propanolamine, iso-propanolamine, 4-amino-1-butanol, 2-amino-1-butanol, 1-amino-2-butanol, ethylenediamine, 1,3-propanediamine, 1,4-butanediamine, 1,6-hexamethylenediamine, or the like. Selection of the secondary amine is not particularly limited, and it can be diethylamine, di-n-propylamine, di-iso-propylamine, di-n-butylamine, di-iso-butylamine, di-sec-butylamine, diethanolamine, di-n-propanolamine, di-iso-propanolamine, or the like. Selection of the tertiary amine is not particularly limited, and it can be triethylamine, tri-n-propylamine, tri-iso-propylamine, tri-n-butylamine, tri-iso-butylamine, triethanolamine, tri-n-propanolamine, tri-iso-propanolamine, or the like.

By preparing a neutralized solution by neutralizing the above-mentioned aqueous solution with an alkaline compound, bis(fluorosulfonyl)imide salt (($FSO_2$)$_2$N.M) and fluorosulfate ($FSO_3$.M) can be produced.

As bis(fluorosulfonyl)imide salt (($FSO_2$)$_2$N.M), bis(fluorosulfonyl)imide sodium salt, bis(fluorosulfonyl)imide potassium salt, bis(fluorosulfonyl)imide lithium salt, or bis(fluorosulfonyl)imide ammonium salt can be produced.

As fluorosulfate ($FSO_3$.M), sodium fluorosulfate, potassium fluorosulfate, lithium fluorosulfate, or ammonium fluorosulfate can be produced.

[Step of Recovering]

Next, bis(fluorosulfonyl)imide salt is recovered from the neutralized solution. In the case where the solubility of the bis(fluorosulfonyl)imide salt is low in the neutralized solution, the bis(fluorosulfonyl)imide salt can be recovered from the neutralized solution by a separation process, such as separation with a separation funnel (separating the bis(fluorosulfonyl)imide salt in liquid state), filtration (separating the bis(fluorosulfonyl)imide salt in solid state), or the like.

In the case where the bis(fluorosulfonyl)imide salt is dissolved in the neutralized solution, the bis(fluorosulfonyl)imide salt can be extracted from the neutralized solution by utilizing an organic solvent. In this extraction with an organic solvent, the bis(fluorosulfonyl)imide salt alone can be selectively separated from the neutralized solution. Selection of the organic solvent used for extracting the bis(fluorosulfonyl)imide salt from the neutralized solution is not particularly limited as long as it dissolves the bis(fluorosulfonyl)imide salt and forms an organic phase separated from the aqueous phase. As the organic solvent forming an organic phase separated from the aqueous phase, acetic acid ester solvents are preferable. In particular, ethyl acetate is more preferable.

A preferable amount of the organic solvent for extracting the bis(fluorosulfonyl)imide salt ranges from 1 to 50 parts by mass corresponding to that of the bis(fluorosulfonyl)imide salt. A more preferable amount of the organic solvent ranges from 10 to 20 parts by mass corresponding to that of the bis(fluorosulfonyl)imide salt. It is not preferable to use less than 10 parts by mass of an organic solvent to that of the bis(fluorosulfonyl)imide salt, since the bis(fluorosulfonyl)imide salt cannot be extracted sufficiently. Using more than 50 parts by mass of the organic solvent to that of the bis(fluorosulfonyl)imide salt is economically wasteful. It is preferable that the amount of the organic solvent used for the extraction falls between the ranges mentioned above, since the bis(fluorosulfonyl)imide salt can be sufficiently extracted.

In the case where the produced bis(fluorosulfonyl)imide salt is in the solid state at room temperature, the bis(fluorosulfonyl)imide salt can be obtained as a crystal by distilling away the organic solvent or the like used for the extraction.

The bis(fluorosulfonyl)imide salt can be produced as explained above.

Compounds having a fluoride-containing anion, such as bis(fluorosulfonyl)imide salt are known as useful anion sources for ion electrical conducting materials, electrolytes, and ion liquids. In the case where the fraction of the bis(fluorosulfonyl)imide salt containing a large amount of fluoride ions as impurities is used, the contaminating fluoride ions cause corrosion of an apparatus and deterioration of plastic. Therefore, it is preferable that the amount of the fluoride ion in the fraction of the bis(fluorosulfonyl)imide is low.

In the conventional method for producing bis(fluorosulfonyl)imide salt as disclosed in NPL3, a part of the bis(fluorosulfonyl)imide salt undergoes hydrolysis in the process where water is distilled away. This hydrolysis of the bis(fluorosulfonyl)imide salt results in formation of the fluoride ions or the like as impurities in the fraction of the bis(fluorosulfonyl)imide salt. Consequently, the recovered fraction of the bis(fluorosulfonyl)imide salt is contaminated with a large amount of impurities. More specifically, the recovered fraction of the bis(fluorosulfonyl)imide salt has included fluoride ions of several hundreds ppm to several thousands ppm as impurities. In NPL3, a purification method with recrystallization using ethanol is also disclosed. However, there was almost no effect on the reduction of the amount of the fluoride ions by the recrystallization.

On the other hand, in the method for producing bis(fluorosulfonyl)imide salt of the present invention, bis(fluorosulfonyl)imide salt is precipitated in an aqueous solution containing bis(fluorosulfonyl)imide salt. In the case where bis(fluorosulfonyl)imide salt is dissolved in a solution, the bis(fluorosulfonyl)imide salt alone is extracted selectively with an organic solvent, and by distilling away the organic solvent, the bis(fluorosulfonyl)imide salt is obtained. Accordingly, there is no need to heat treat bis(fluorosulfonyl)imide salt in water. Therefore, the occurrence of hydrolysis of bis(fluorosulfonyl)imide salt by water is extremely low, and the amount of impurities in the fraction of bis(fluorosulfonyl)imide salt can be reduced. Due to reasons described above, highly pure bis(fluorosulfonyl)imide salt can be recovered.

The amount of fluoride ions contained in the fraction of bis(fluorosulfonyl)imide salt can be measured for example by the ion-chromatography method. The measurement of the content of fluoride ions can be performed as described below.

First, a sample for measurement is prepared by dissolving 0.5 g of the specimen in the 50 mL of ion-exchange water. Then, the measurement of the content of fluoride ion in the sample is performed using for example the ion-chromatography system ICS-2000 manufactured by DIONEX corporation (column: IonPacAS19, detector: conductivity detector). The elution solution is a potassium hydroxide solution in the concentration of 20 mmol/L (flow rate is 1.0 mL/min).

[Method for Producing Fluorosulfate]

The method for producing fluorosulfate of the present invention includes, a step of dissolving, in which a mixed liquid containing bis(fluorosulfonyl)imide and fluorosulfonic acid is dissolved in water to prepare an aqueous solution (step of preparing an aqueous solution), a step of neutralizing, in which the aqueous solution is neutralized by an alkali compound to prepare a neutralized solution (step of preparing a neutralized solution), and a step of recovering fluorosulfate, in which fluorosulfate is recovered from the neutralized solution (step of recovering). Since, the step of preparing an aqueous solution and the step of preparing a neutralized solution are identical to those explained in the method for producing bis(fluorosulfonyl)imide salt, details of the steps are omitted.

[Step of Recovering]

Fluorosulfate is recovered from the neutralized solution prepared in the step of preparing a neutralized solution. Generally, the solubility of fluorosulfate in the neutralized solution is low. Thus, it is often the case that fluorosulfate is precipitated as a solid from the neutralized solution. Therefore, by applying a separation process such as filtration or the like to the neutralized solution, fluorosulfate can be recovered from the neutralized solution.

In the case where the solubility of the fluorosulfate is high, fluorosulfate and bis(fluorosulfonyl)imide salt can be separated by applying a separating process appropriately selected from those described in the step of recovering bis(fluorosulfonyl)imide salt described above.

[Method for Producing bis(fluorosulfonyl)imide onium salt]

The method for producing bis(fluorosulfonyl)imide onium salt of the present invention includes, a step of dissolving, in which a mixed liquid containing bis(fluorosulfonyl)imide and fluorosulfonic acid is dissolved in water to prepare an aqueous solution (step of preparing an aqueous solution), a step of neutralizing, in which the aqueous solution is neutralized by an alkali compound to prepare a neutralized solution (step of preparing a neutralized solution), and a step of adding an onium compound to the neutralized solution (step of adding an onium compound). Since the step of preparing an aqueous solution and the step of preparing a neutralized solution are identical to those explained in the method for producing bis(fluorosulfonyl)imide salt, details of the steps are omitted.

[Step of Adding an Onium Compound]

An onium compound is added to the neutralized solution prepared in the step of preparing the neutralizing solution. By the addition of an onium compound, salt substitution occurs between the produced bis(fluorosulfonyl)imide salt ($(FSO_2)_2N.M$) and the onium compound. As a result, an ionic compound made of an anion of bis(fluorosulfonyl)imide ($(FSO_2)_2N^-$) and the onium salt is produced.

Selection of the onium compound is not particularly limited. Salts including onium cations, halogen ions, nitrate ions, sulfate ions, phosphate ions, perchlorate ions, methane sulfate ions, toluene sulfate ions, and the like are given as examples.

Selection of the onium cation is not particularly limited, as long as it is a cation having at least one organic group that is formed by a coordination between a compound with a lone electron pair and a cationic atomic group. Nitrogen, sulfur, oxygen, phosphorus, selenium, tin, iodine, and antimony are examples of compounds with a lone electron pair. As onium ions that can be used in the present invention and belong to the symmetric ammonium cation group, tetramethylammonium cations, tetraethylammonium cations, and tetrapropylammonium cations are examples. As onium ions that can be used in the present invention, belong to the ammonium cation group, and the number of carbon atoms in the shortest substituent group corresponds to 50% or higher and less than 100% of the number of carbon atoms in the longest substituent group (referred as pseudo-symmetric hereinafter), ethyltrimethylammonium cations, vinyltrimethylammonium cations, triethylmethylammonium cations, triethylpropylammonium cations, diethyldimethylammonium cations, tributylethylammonium cations, triethylisopropylammonium cations, N,N-dimethylpyrrolidinium cations, N-methyl-N-ethylpyrrolidinium cations, triethylmethoxymethylammonium cations, and the like are examples. As onium ions that can be used in the present invention and belong to the asymmetric ammonium cation group, trimethylpropylammonium cations, trimethylisopropylammonium cations, butyltrimethylammonium cations, allyltrimethylammonium cations, hexyltrimethylammonium cations, octyltrimethylammonium cations, dodecyltrimethylammonium cations, triethylmethoxyethoxymethylammonium cations, dimethyldipropylammonium cations, and the like are examples. As onium ions that can be used in the present invention and belong to the divalent ammonium cation group, hexamethonium cations and the like are exemplified. As onium ions that can be used in the present invention and belong to the symmetric imidazolium cation group, 1,3-dimethylimidazolium cations, 1,3-diethylimidazolium cations, 1,3-dipropylimidazolium cations, 1,3-dipropylimidazolium cations, and the like are examples. As onium ions that can be used in the present invention and belong to the asymmetric imidazolium cation group, 1-ethyl-3-methylimidazolium cations, 1-methyl-3-propylimidazolium cations, 1-butyl-3-methylimidazolium cations, 1-isopropyl-3-propylimidazolium cations, 1-tert-butyl-3-isopropylimidazolium cations, and the like are examples. As onium ions that can be used in the present invention and belong to the pyridinium cation group, N-ethylpyridinium cations, N-butylpyridinium cations, and the like are examples. As onium ions that can be used in the present invention and belong to the symmetric sulfonium cation group, trimethylsulfonium cations, triethylsulfonium cations, tributylsulfonium cations, and the like are examples. As onium ions that can be used in the present invention and belong to the pseudo-symmetric sulfonium cation group, eiethilmetilsulfonium cations and the like are exemplified. As onium ions that can be used in the present invention and belong to the asymmetric sulfonium cation group, dimethylpropylsulfonium cations, dimethylhexylsulfonium cations, and the like are examples. As onium ions that can be used in the present invention and belong to the symmetric phosphonium cation group, tetramethylphosphonium cations, tetraethylphosphonium cations, tetrapropylphosphonium cations, tetrabutylphosphonium cations, tetraoctylphosphonium cations, tetraphenylphosphonium cations, and the like are examples. As onium ions that can be used in the present invention and belong to the pseudo-symmetric phosphonium cation group, trimethilethyl phosphonium cations, triethylmethylphosphonium cations, and the like are examples. As onium ions that can be used in the present invention and belong to the asymmetric phosphonium cation group, hexyltrimethylphosphonium cations, trimethyloctylphosphonium cations, and the like are examples.

In this embodiment of the present invention, it is preferable to use the onium salts belonging to the imidazole system or the ammonium system. Bis(fluorosulfonyl)imide onium salt can be produced as explained above.

As explained above, according to the method for producing bis(fluorosulfonyl)imide salt of the present invention, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By recovering bis(fluorosulfonyl)imide salt from the neutralized solution, a highly pure bis(fluorosulfonyl)imide salt can be obtained safely and easily.

In the case where the bis(fluorosulfonyl)imide salt is dissolved in the neutralized solution, the bis(fluorosulfonyl)imide salt can be extracted from the neutralized solution by an organic solvent. In this way, the bis(fluorosulfonyl)imide salt alone can be selectively separated from the neutralized solution.

According to the method for producing fluorosulfate of the present invention, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By recovering fluorosulfate from the neutralized solution, a highly pure fluorosulfate can be obtained safely and easily.

In the case where the fluorosulfate is precipitated in the neutralized solution, the fluorosulfate can be separated by filtering the neutralized solution. In this way, the fluorosulfate alone can be selectively separated from the neutralized solution.

According to the method for producing bis(fluorosulfonyl)imide onium salt of the present invention, first, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By adding an onium compound to the neutralized solution and changing salts of the bis(fluorosulfonyl)imide salt in the neutralized solution, the bis(fluorosulfonyl)imide onium salt can be obtained safely and easily.

EXAMPLES

The advantageous effect of the present invention is explained in detail with Examples below. The present invention is not limited by configuration detailed in the Examples.

Example 1

First, 3.2 kg of fluorosulfonic acid was placed in a reaction container whose internal volume is 5 L. The reaction container was made of polytetrafluoroethylene (PTFE) and equipped with a mixer and a thermometer. Then, 800 g of urea was added to the fluorosulfonic acid in the container little by little with cooling to prepare a fluorosulfonic acid solution containing urea.

In another reaction container whose internal volume was 5 L, 2.4 kg of fluorosulfonic acid and 80 g of bis(fluorosulfonyl)imide were placed. The surface of the container is made of stainless and coated with PTFE. The container was equipped with a mixer, a thermometer, and a gas flowmeter. Then, the fluorosulfonic acid solution containing urea was dripped in the container with a metering pump at the rate of 525 g/Hr, while the content of the container was heated to 120° C.

Once the dripping started, gaseous carbon dioxide was generated. At the endpoint of the dripping, the volume of the gas reached 299 L. The final reaction solution was cooled down to room temperature. Then, 15 kg of water was dripped into the final reaction solution little by little, having the water dissolved in the final reaction solution. Then, 3.6 kg of potassium carbonate was added to the solution to neutralize the solution and the pH of the solution increased to 9. Then, precipitated crystals was obtained by filtering the neutralized solution. By drying the crystals at 60° C., 4.4 kg of bis(fluorosulfonyl)imide potassium salt was obtained. The solution passing through the filter was extracted with 7 kg of ethyl acetate twice, and with 2 kg of ethyl acetate once.

Then, the ethyl acetate phase was washed with water, the ethyl acetate was distilled away, and 1081 g of bis(fluorosulfonyl)imide potassium salt was obtained as residue (the recovery based on the precursor urea was 37%). The content of fluoride ions in the specimen was measured with the ion-chromatography system ICS-2000 manufactured by DIONEX corporation (column: IonPacAS19, detector: conductivity detector). The elution solution was potassium hydroxide solution in the concentration of 20 mmol/L (flow rate is 1.0 mL/min) Based on the measurement, the content of fluoride ion in the sample was 3 ppm. The boiling point of the obtained bis(fluorosulfonyl)imide potassium salt was 103 to 104° C. When the samples was analyzed with $^{19}$F-NMR analysis, the peak at 53.5 ppm was detected (solvent: DMSO-d, internal standard compound: $CFCl_3$).

Example 2

Example of Ammonium Salt

The final reaction solution that was cooled down to room temperature was obtained as in the Example 1. The final reaction solution was dissolved in 15 kg of water. Then, the solution was neutralized with 2.0 kg of 28% aqueous ammonia, having the pH of the solution increased to 7. Then, the neutralized solution was extracted with 7 kg of ethyl acetate twice and with 2 kg of ethyl acetate once. The resulting ethyl acetate phase was washed with water. Then, the ethyl acetate in the extracting phase was distilled away. In this way, 792 g of bis(fluorosulfonyl)imide ammonium salt was obtained as residue (the recovery based on the precursor urea was 30%). The content of fluoride ion in the obtained bis(fluorosulfonyl)imide ammonium salt was 3 ppm. The boiling point of the sample was 85 to 88° C.

Example 3

Example Using Li

One hundred grams of the final reaction solution prepared as described in the Example 1 was dissolved in 200 g of water. Then, the solution was neutralized with 46 g of lithium carbonate, causing the pH of the solution to increase to 7. After filtering out the excess lithium carbonate, the aqueous phase was extracted with 100 g of ethyl acetate twice, and with 30 g of ethyl acetate once. The obtained ethyl acetate phase was washed with 30 g of ion exchange water. Then, the ethyl acetated in the extracting solution was distilled away. In this way, 14.5 g of bis(fluorosulfonyl)imide lithium salt was obtained as residue (the recovery based on the precursor urea was 35%). The content of the fluoride ion in the obtained bis(fluorosulfonyl)imide lithium salt was 8 ppm.

Example 4

Two hundred grams of the final reaction solution prepared as described in the Example 1 was dissolved in 800 g of water. Then, the solution was neutralized with 52 g of potassium carbonate, having the pH of the solution increased to 7. The precipitated fluorosulfate potassium salt was filtered out. Then, an aqueous solution dissolving 37 g of tetrapropylammonium bromide was dripped into the filtered neutralized solution. Once the dripping started, crystals of bis(fluorosulfonyl)imide tetrapropylammonium salt were precipitated out. After recovering the precipitated crystals by filtration, they were dried in a drier set at 60° C. In this way, 48 g of bis(fluorosulfonyl)imide tetrapropylammonium salt was obtained (the recovery based on the precursor urea was 30%). The content of the fluoride ion in the obtained bis(fluorosulfonyl)imide tetrapropylammonium salt was 1 ppm. The boiling point of the obtained sample was 140 to 141° C.

Example 5

Two hundred grams of the final reaction solution prepared as described in the Example 1 was dissolved in 800 g of water. Then, the solution was neutralized with 51 g of potassium carbonate, causing the pH of the solution to increase to 7. The precipitated fluorosulfate potassium salt was filtered out. When 31 g of 1-butyl-3-methylimidazoliumbromide was added to the filtered solution, bis(fluorosulfonyl)imide 1-butyl-3-methylimidazoliumbromide salt was separated from the filtered solution. The separated organic phase was washed with water. Then, by drying the organic phase, 45 g of bis(fluorosulfonyl)imide 1-butyl-3-methylimidazoliumbromide salt was obtained (the recovery based on the precursor urea was 32%). The content of the fluoride ion in the obtained bis(fluorosulfonyl)imide 1-butyl-3-methylimidazoliumbromide salt was 1 ppm.

Comparative Example

The final reaction solution prepared as in the Example 1 was distilled under reduced pressure to obtain a mixture consisting of fluorosulfate and bis(fluorosulfonyl)imide. Six hundred forty five grams of this mixture was dissolved in 3230 g of methylene chloride. Then, 170 g of sodium chloride was added to the solution, producing bis(fluorosulfonyl)imide sodium salt. Then, the produced bis(fluorosulfonyl)imide sodium salt was filtered. Methylene chloride in the filtered solution was distilled away. Then, 326 g of bis(fluorosulfonyl)imide sodium salt was obtained by further distilling the residual liquid under ordinary pressure. This bis(fluorosulfonyl)imide sodium salt was dissolved in 978 g of water, and neutralized by 154 g of potassium carbonate, causing the pH of the solution to increase to 7. Then, by distilling away the water in the neutralized solution, 313 g of bis(fluorosulfonyl)

imide potassium salt was obtained. The content of fluoride ion in the specimen was 354 ppm.

While preferred embodiments of the invention have been described above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

INDUSTRIAL APPLICABILITY

The present invention relates to a method for producing bis(fluorosulfonyl)imide salt, a method for producing fluorosulfate, and a method for producing bis(fluorosulfonyl)imide onium salt. In the method for producing bis(fluorosulfonyl) imide salt, the method for producing fluorosulfate, and the method for producing bis(fluorosulfonyl)imide onium salt of the present invention, an aqueous solution is prepared by dissolving a mixed liquid containing bis(fluorosulfonyl)imide and fluorosulfonic acid in water. Then, the aqueous solution is neutralized with an alkaline compound, producing bis(fluorosulfonyl)imide salt and fluorosulfate. By adding an onium compound to the neutralized solution and exchanging salts, bis(fluorosulfonyl)imide onium salt can be obtained safely and easily.

The invention claimed is:

1. A method for producing bis(fluorosulfonyl)imide salt comprising:
    a step of dissolving, in which a mixed liquid containing bis(fluorosulfonyl)imide and fluorosulfonic acid is dissolved in water to prepare an aqueous solution;
    a step of neutralizing, in which the aqueous solution is neutralized by an alkali compound to prepare a neutralized solution; and
    a step of recovering bis(fluorosulfonyl)imide salt, in which bis(fluorosulfonyl)imide salt is recovered from the neutralized solution;
    wherein the total amount of the water dissolving the mixed liquid in the step of dissolving is 1 to 50-fold by mass relative to a mass of the mixed liquid.

2. A method for producing bis(fluorosulfonyl)imide salt according to claim 1,
    wherein, bis(fluorosulfonyl)imide salt is recovered in the step of recovering bis(fluorosulfonyl)imide salt by extracting the neutralized solution with an organic solvent.

3. A method for producing bis(fluorosulfonyl)imide salt according to claim 1,
    wherein, the mixed liquid dissolved in water in the step of dissolving is a reaction liquid produced by a reaction between urea and fluorosulfonic acid.

4. A method for producing bis(fluorosulfonyl)imide salt according to claim 1,
    wherein, the alkaline compound used in the step of neutralizing is one compound selected from the group consisting of MOH, $M_2CO_3$, $MHCO_3$, ammonia, and amine,
    wherein M in the chemical formulae, represents one selected from the group consisting Na, K, Li, and ammonium cation.

5. A method for producing bis(fluorosulfonyl)imide salt according to claim 1,
    wherein, a content amount of fluorine ion in bis(fluorosulfonyl)imide salt after the step of recovery is 100 ppm or less.

6. A method for producing bis(fluorosulfonyl)imide salt according to claim 1,
    wherein, a content amount of fluorine ion in bis(fluorosulfonyl)imide salt after the step of recovery is 20 ppm or less.

7. A method for producing bis(fluorosulfonyl)imide salt according to claim 2,
    wherein, the alkaline compound used in the step of neutralizing is one compound selected from the group consisting of MOH, $M_2CO_3$, $MHCO_3$, ammonia, and amine,
    wherein M in the chemical formulae, represents one selected from the group consisting Na, K, Li, and ammonium cation.

8. A method for producing bis(fluorosulfonyl)imide salt according to claim 2,
    wherein, a content amount of fluorine ion in bis(fluorosulfonyl)imide salt after the step of recovery is 100 ppm or less.

9. A method for producing bis(fluorosulfonyl)imide salt according to claim 2,
    wherein, a content amount of fluorine ion in bis(fluorosulfonyl)imide salt after the step of recovery is 20 ppm or less.

* * * * *